United States Patent
Takano et al.

[11] Patent Number: 5,300,515
[45] Date of Patent: Apr. 5, 1994

[54] CARBAMIC ACID DERIVATIVES AND METHOD FOR PREPARING THE SAME

[75] Inventors: Yasuo Takano, Kazo; Masanori Takadoi, Kuki; Takashi Hirayama, Washimiya; Atsuhiro Yamanishi, Nogi, all of Japan

[73] Assignee: Kyorin Pharmaceutical Co., Ltd., Tokyo, Japan

[21] Appl. No.: 824,983

[22] Filed: Jan. 24, 1992

[30] Foreign Application Priority Data

Jan. 31, 1991 [JP] Japan .................. 3-031922

[51] Int. Cl.⁵ .......................... C07D 211/68
[52] U.S. Cl. .................... 514/318; 546/193; 546/194
[58] Field of Search .......... 546/222, 194, 193; 514/318

[56] References Cited

U.S. PATENT DOCUMENTS

| | | | |
|---|---|---|---|
| 3,031,455 | 4/1967 | Holysz | 546/222 |
| 4,223,147 | 9/1980 | Oertel et al. | 546/222 |
| 4,558,131 | 12/1985 | Leppard et al. | 546/222 |
| 4,673,683 | 6/1987 | Buschmann et al. | 546/222 |

FOREIGN PATENT DOCUMENTS

| | | |
|---|---|---|
| 0169139 | 1/1986 | European Pat. Off. |
| 2000136 | 1/1979 | United Kingdom |
| 2021108 | 11/1979 | United Kingdom |

OTHER PUBLICATIONS

Patent Abstracts of Japan, vol. 12, No. 446, (C-546) [3293], Nov. 24, 1988, & JP-A-63-170356, Jul. 14, 1988, T. Tamura, et al., "Aniline Derivative and Production Thereof".

*Primary Examiner*—Alan L. Rotman
*Assistant Examiner*—Raymond Covington
*Attorney, Agent, or Firm*—Oblon, Spivak, McClelland, Maier & Neustadt

[57] ABSTRACT

Anti-dementia medicaments comprising a carbamic acid derivative or their pharmaceutically acceptable acid addition salts having an anti-amnesic activity as an active ingredient are provided. The carbamic acid derivatives are represented by a general formula (1)

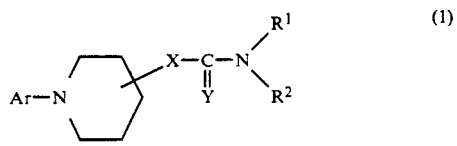

wherein Ar denotes an aromatic heterocyclic ring which may have at least one substituent or its benzene-condensed ring, or phenyl group which may have at least one substituent, $R^1$ denotes hydrogen atom or lower alkyl group, $R^2$ denotes lower alkyl group which may be substituted with halogen atom, phenyl group which may have at least one substituent, naphthyl group, or five- or six-membered heterocyclic ring and its benzene-condensed ring, X and Y, which may be the same or different, denote sulfur atom or oxygen atom.

2 Claims, No Drawings

CARBAMIC ACID DERIVATIVES AND METHOD FOR PREPARING THE SAME

BACKGROUND OF THE INVENTION

The present invention concerns carbamic acid derivatives or their phamaceutically acceptable acid addition salts having anti-amnesic activity, methods for preparing them, intermediates for preparing them, and anti-dementia comprising the carbamic acid derivatives or their pharmaceutically acceptable acid addition salts as an active ingredient.

Recently, with elongation of average life, dementia diseases such as Alzheimer type senile dementia have arisen as a great problem in medical as well as social field.

Patients of dementia show symptom such as loss of intellectual ability, disturbance of memory, disturbance of abstract thinking, verbal aphasia, apraxia, disorientation and so on, and the disturbance of fundamental functions lies in that of formation of memory or expressing ability of hold memory.

However, up to now there have been hardly any medicament to cure it effectively and hence rapid development of remedy thereof has been longed.

Then, for compounds analogous to carbamic acid derivatives of the present invention, there have been known compounds of a general formula (10)

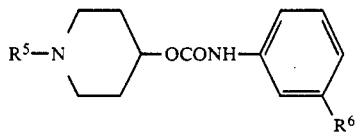

wherein $R^5$ denotes ethyl, propyl or butyl group and $R^6$ denotes hydroxy, butoxy, pentoxy, hexyloxy or heptoxy group, which is described in Pharmazie, 44,25, (1989), those of general formulae (11) and (12)

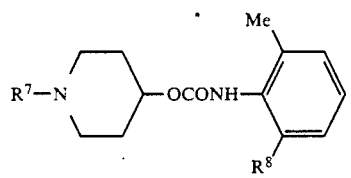

wherein $R^7$ denotes methyl, ethyl, n-propyl, iso-propyl or t-butyl group and $R^8$ denotes methyl group or chlorine atom,

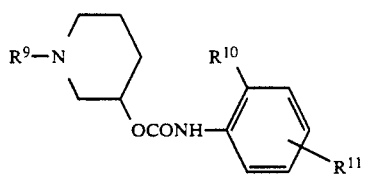

wherein $R^9$ denotes methyl, ethyl, n-propyl, iso-propyl, n-butyl, t-butyl group, $R^{10}$ denotes hydrogen atom or methyl group, and $R^{11}$ denotes methyl group substituted at o-position, halogen atom substituted at each position of o-, m- or p-position, methoxy group substituted at p-position and acetyl group substituted at p-position, having local anesthesia function described in J. Med. Chem., 14, 710 (1971), those of a general formula (13)

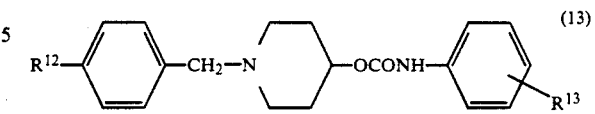

wherein $R^{12}$ denotes a hydrogen atom, methyl group or chlorine atom and $R^{13}$ denotes a chlorine atom or methyl group substituted at o-, m- or p-position, synthesized for a comparative compound in application research of agent of anti-arterial sclerosis described in J. Pharma. Sci., 59, 303 (1970), those of general formula (14)

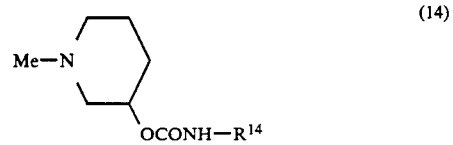

wherein $R^{14}$ denotes methyl, ethyl, n-propyl, n-butyl or phenyl group, having inhibitory action against cholinesterase described in Egypt. J. Pharma. Sci., 26, 267 (1985), and so forth. However, it is unknown at all that these carbamic acid derivatives display anti-amnesia action, and further these are different from carbamic acid derivatives of the present invention in the structure thereof.

The object of the present invention lies in providing a medicament for improving disturbance of memory which is effective to symptoms of dementia and having high safety factor, in considering the present status of patients of dementia as mentioned above.

SUMMARY OF THE INVENTION

As the result of diligent study for aiming at development of novel anti-dementia medicaments, the inventors of the present invention have found that carbamic acid derivatives of the present invention and acid addition salts thereof have an excellent anti-amnesic action. That is, the inventors of the present invention have found that carbamic acid derivatives represented by a general formula (1)

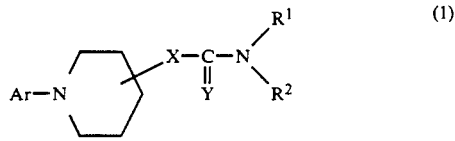

wherein Ar denotes an aromatic heterocyclic ring or its benzene-condensed ring which may have at least one substituent or phenyl group which may have at least one substituent, $R^1$ denotes hydrogen atom or lower alkyl group, $R^2$ denotes lower alkyl group which may be substituted with halogen atom, phenyl group which may have at least one substituent, naphthyl group, or five- or six-membered heterocyclic ring or its benzene-condensed ring, and X and Y, being same or different, denote sulfur atom or oxygen atom or their acid addition salts have a surprisingly excellent anti-amnesia activity, and have come to complete the present invention.

In the general formula (1) of the present invention, for the aromatic heterocyclic ring or its benzene-condensed ring which may have at least one substituent, a group including 1-3 hetero-atom such as for example pyridyl, pyrimidyl, pyridazyl, pyrazyl, quinolyl and benzothiazolyl can be exemplified, and for the lower alkyl group, a straight or branched chain having 1-6 carbon number such as methyl, ethyl, n-propyl and iso-propyl can be exemplified.

For the substituent in the aromatic heterocyclic ring or its benzene-condensed ring which may have at least one substituent and in the phenyl group which may have at least one substituent, naphthyl group, or five- or six-membered heterocyclic ring or its benzene-condensed ring, a halogen atom, lower alkyl group which may be substituted with halogen atom, lower alkoxy group, cyano group, nitro group, amino group wherein this amino group may be substituted with acyl group, for example acetyl group etc., or may be substituted with 1-2 lower alkyl group, hydroxyl group wherein this hydroxyl group may be substituted with acyl group, for exmaple acetyl group etc., lower alkylthio group, lower alkoxycarbonyl, benzene ring and so on can be exemplified.

For the halogen atom, fluorine, chlorine, bromine and iodine atom can be exemplified, for the lower alkoxy group, a straight or branched chain of 1-4 carbon number such as methoxy, ethoxy or propoxy group, and for the lower alkoxycarbonyl group, a group of 1-4 carbon number such as methoxycarbonyl or ethoxycarbonyl can be exemplified.

The five- or six-membered heterocyclic ring and its benzene-condensed ring stands for a saturated or unsaturated monocyclic group and its benzene-condensed ring which can be exemplified by, for example, piperidyl, piperazyl, morphoryl, furanyl, thienyl, pyrrolidyl, pirazolyl, imidazolyl, oxazolyl, thiazolyl, pyridyl, pyrimidyl, pyridazyl, pyrazyl, benzofuranyl, benzothienyl, indolyl, benzimidazolyl, benzoxazolyl, benzothiazolyl, quinolyl, isoquinolyl, quinazolyl, quinoxalyl, cinnolyl and so on.

The acid addition salts stand for a pharmaceutically acceptable salt such as, for example, hydrochloric acid, citric acid, succinic acid, fumaric acid or maleic acid.

For a protecting group of the amino group, for example, a lower acyl group such as acetyl or propionyl group, an alkoxycarbonyl group such as methoxy carbonyl or t-butoxy carbonyl group can be exemplified.

For an eliminating group, for example, a halogen atom such as fluorine, chlorine, bromine or iodine, sulfonyloxy group such as p-toluenesulfonyloxy group or methanesulfonyloxy group.

For a condensing agent, for example, carbonyldiimidazoles such as N,N'-carbonyldiimidazole (CDI), N,N'-succinimidyl carbonate (DSC) or N,N'-thiocarbonyldiimidazole (TCDI), phosgene or its analogue such as, for example, trichloromethylchloroformate or triphosgene can be exemplified.

The compound of the present invention can be prepared by the following preparative methods.

A compound represented by the general formula (1) can be synthesized through the two processes below with employment of a compound represented by a general formula (2)

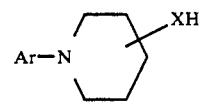

(2)

wherein Ar and X are as mentioned above.

(A) It can be synthesized by allowing a compound represented by the general formula (2) and a corresponding amino compound to react in a suitable solvent such as, for exmaple, methylene chloride, chloroform or tetrahydrofuran at a temperature of −20° C. - room temperature in the presence of a condensing agent for 2-4 hours.

Herein, the condensing agent means allowing phosgene or its analogue (for example trichloromethylchloroformate, triphosgene and so on) to react in the presence of a suitable base, for example, triethylamine etc., or introducing carbonyl group of urethane moiety with employing N,N'-carbonyldiimidazole (CDI), N,N'-succinimidyl carbonate (DSC) or N,N'-thiocarbonyldiimidazole (TCDI).

(B) It can be synthesized by allowing a compound represented by the general formula (2) to react with a corresponding isocyanic acid ester or isothiocyanic acid ester in a suitable solvent, for example, ether, benzene, tetrahydrofuran, dichloromethane, dimethylformamide etc. or without solvent at a reaction temperature of room temperature - 80° C., if desired, in the presence of a suitable base such as, for example, sodium hydride or triethylamine, for 1-3 hours.

Herein, the corresponding isocyanic acid ester or isothiocyanic acid ester includes also isocyanic acid ester or isothiocyanic acid ester synthesized in situ through Curtius rearrangement after allowing a corresponding carboxylic acid or thiocarboxylic acid to react with thionyl chloride, sodium azide successively, or with diphenylphosphorye azide (DPPA).

A part of the compounds represented by the general formula (2) is publicly known and can be synthesized according to Japanese Laid-open Publication No. Hei 2-83369 or Heterocycles, 16(11), 1883 (1981).

The compound represented by the general formula (1) can be also synthesized by allowing a compound of a general formula (5) to react with a compound of a general formula (6) in a suitable solvent, for example ethanol, isoamyl alcohol, tertbutanol etc., in the presence of a suitable base, for example sodium hydrogen carbonate, potassium carbonate and so on at a temperature of room temperature - boiling point of the solvent for 5-20 hours.

At this time, the reaction can be enhanced by further adding sodium acetate, potassium iodide or sodium iodide.

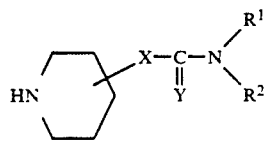

(5)

Ar—Z (6)

wherein Ar, $R^1$, $R^2$, X and Y are as mentioned before and Z denotes an eliminating group.

Herein, the compound represented by the general formula (5) can be synthesized according to the following scheme.

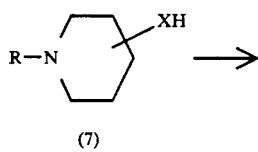

(7)

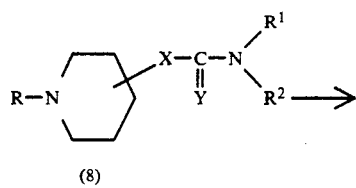

(8)

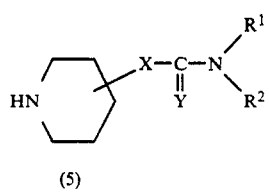

(5)

wherein R denotes a protecting group of amino group, and $R^1$, $R^2$, X and Y are as mentioned before. That is, the compound represented by the general formula (5) can be synthesized by converting a compound represented by the general formula (7) corresponding to a compound of hydroxy- or mercapto-piperidine, nitrogen atom of which is protected, into a compound of the general formula (8) according to the beforementioned method of (A) or (B), followed by eliminating the protecting group.

Herein, the reaction of eliminating the protecting group can be conducted by effecting the reaction in a suitable solvent, for example ethanol, tetrahydrofuran, dimethylformamide and so on in the presence of acid such as, for example, hydrochloric acid or sulfuric acid at a temperature of room temperature - boiling temperature of the solvent for 1-10 hours.

Furthermore, the compounds of the general formula (1), (2), (5), (7), (8) and (9) may have asymmetric carbon depending on the position of substituent on piperidine ring and so there are two kinds of optical isomer basing on said asymmetric carbon, but each of them or their mixture are all involved in the scope of the invention.

Further, if pharmaceutically acceptable acid addition salts of the compound represented by the general formula (1) are required, those of the synthesized carbamic acid ester can be obtained by, for example, the reaction with inorganic acid such as hydrochloric acid or with organic acid such as succinic acid.

EXAMPLE

Then, examples of the present invention including preparative examples thereof are described as follows to explain the present invention further in more details.

Example 1

[4-(1-(4-pyridyl)piperidyl)] 1-naphthylcarbamate

Into a suspension of sodium hydride (320 mg) in N,N-dimethylformamide (30 ml) was dropwise added a solution of 1-(4-pyridyl)-4-piperidinol (1.2 g) in N,N-dimethylformamide at 0° C. under argon atmosphere and the mixture was further stirred for 30 minutes. A solution of 1-naphthylisocyanate (1.14 g) in N,N-dimethylformamide (10 ml) was added thereto and the mixture was stirred at room temperature for about 5 hours and 30 minutes. After the stirring, the reaction mixture was poured into water, extracted with methylene chloride, dried over anhydrous magnesium sulfate and then the solvent was distilled off under the reduced pressure to give crude crystal. This was recrystallized (acetonitrile-N,N-dimethylformamide) to give the title compound 550 mg of pale yellow powder crystal.

Melting point 233°–234° C.
Elementary analysis for $C_{21}H_{21}N_3 O_2$:
Calculated value C: 72.60, H: 6.09, N: 12.10.
Observed value C: 72.57, H: 6.07, N: 12.20.

Example 2

[4-(1-4-pyridyl)piperidyl)] 4-chlorophenylcarbamate

In a solvent of benzene, 1-(4-pyridyl)-4-piperidinol (400 mg) was heated and refluxed with 4-chlorobenzoic acid (350 mg), DPPA (0.48 ml) and triethylamine (0.31 ml) for about 6 hours.

After cooled, the mixture was distilled off under the reduced pressure to give colorless residue. This was recrystallized (acetonitrile) to give 280 mg of the title compound of colorless needle crystal.

Melting point 240°–241° C.
Elementary analysis for $C_{17}H_{18}ClN_3 O_2$:
Calculated value C: 61.54, H: 5.47, N: 12.66.
Observed value C: 61.57, H: 5.44, N: 12.59.

Example 2A

[4-(1-(4-pyridyl)piperidyl)] 4-chlorophenylcarbamate

Into a solution of 4-piperidyl 4-chlorophenylcarbamate (10.11 g) in isoamyl alcohol (200 ml) were added 4-chloropyridine hydrochloride (5.95 g) and sodium hydrogen carbonate (6.67 g) successively at room temperature, and the mixture was refluxed with heating under argon atmosphere for about 8 hours. After cooled, the mixture was filtered and the residue was washed with warm ethanol. The filtrate was concentrated and extracted with methylene chloride in a condition of alkali. This organic layer was dried over anhydrous sodium sulfate and the solvent was distilled off under reduced pressure. The obtained residue was crystallized with addition of ethyl acetate, which was then recrystallized to give 3.8 g of the title compound. The instrumental analysis data of this compound were identical with those of Example 2.

Example 2B

[4-(1-(4-pyridyl)piperidyl)] 4-chlorophenylcarbamate hydrochloride

Into a mixture (40 ml) of ethyleneglycol and DMF was dissolved [4-(1-(4-pyridyl) piperidyl)] 4-chlorophenylcarbamate (500 mg), and the mixture was cooled at 0° C. and was introduced with hydrogen chloride gas for 30 minutes. Then, this was distilled off under reduced pressure and precipitated crystal was recrystallized from ethanol to give 250 mg of the title compound.

Melting point 268°–270° C.
Elementary analysis for $C_{17}H_{18}ClN_3 O_2 \cdot HCl$:
Calculated value C: 55.45, H: 5.20, N: 11.41.
Observed value C: 55.31, H: 5.15, N: 11.28.

Example 3

[4-(1-(4-pyridyl)piperidyl)] N-methyl-4-chlorophenylcarbamate

Into a solution of N-methyl-4-chloroaniline (1.02 ml) in methylene chloride (20 ml) was dropwise added trichloromethylchloroformate (0.66 ml) at 0° C. under argon atmosphere. After the mixture was stirred at 0° C. for 1.5 hours, the mixture was added with triethylamine (1.17 ml) and then stirred at 0° C. for 1 hour. Afterwards, the mixture was dropwise added with a solution of 1-(4-pyridyl)-4-piperidinol (1.5 g) in methylene chloride (15 ml), further added with triethylamine (1.17 ml), and react at 0° C. for 20 minutes, at room temperature for 1 hour after returning to room temperature and further by refluxing with heating for 2 hours. The reaction mixture was poured into water and extracted with methylene chloride. This organic layer was dried over anhydrous sodium sulfate, the solvent was distilled off under reduced pressure, and the obtained residue was purified through column chromatography (alumina, ethyl acetate: n-hexane=5:3). The obtained crude crystal was washed with petroleum ether to give 1.27 g of the title compound of colorless powder crystal.

Melting point 76°–79° C.
Elementary analysis for $C_{18}H_{20}ClN_3 O_2 \cdot 2/5H_2O$:
Calculated value C: 61.24, H: 5.94, N: 11.90.
Observed value C: 61.28, H: 5.86, N: 12.05.

Example 4

[4-(1-(4-pyridyl)piperidyl)] phenylcarbamate

Into a solution of 4-piperidylphenylcarbamate (2 g) in isoamyl alcohol (50 ml) were added 4-chloropyridine hydrochloride (1.4 g), sodium iodide (1.4 g) and sodium hydrogen carbonate (1.6 g) successively at room temperature, and the mixture was refluxed with heating under argon atmosphere for about 12 hours. After cooled, the mixture was added with water to terminate the reaction and extracted with methylene chloride in condition of alkali. This organic layer was dried over anhydrous sodium sulfate, the solvent was distilled off under reduced pressure and the obtained residue was purified through column chromatography (alumina, ethyl acetate). The obtained crude crystal was. recrystallized from a mixture of ethyl acetate and ethanol to give 850 mg of the title compound of Dale yellow powder crystal.

Melting point 215°–216° C.
Elementary analysis for $C_{17}H_{19}N_2 O_2$:
Calculated value C: 68.67, H: 6.44, N: 14.13.
Observed value C: 68.40, H: 6.42, N: 14.16.

Example 5–56

According to the same method as in Example 1–4, the following compounds were obtained.

$$Ar-N\underset{\phantom{X}}{\bigcirc}-X-\underset{\underset{Y}{\|}}{C}-N\overset{R^1}{\underset{R^2}{\diagdown}}$$

| Example | Ar | R¹ | R² | X | Y | M.P. (Solv.) | ANAL. [Calcd. (%)/Found (%)] or Mass (m/e) |
|---|---|---|---|---|---|---|---|
| 5 | 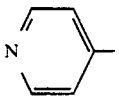 | H | 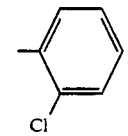 | O | O | 136~137° C. (n-C₆H₁₄:AcOEt) | C₁₇H₁₈ClN₃O₂ C: 61.54 H: 5.47 N: 12.66 C: 61.71 H: 5.47 N: 12.37 |
| 6 | 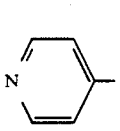 | H | 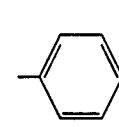 | O | O | 234~235° C. (n-C₆H₁₄:AcOEt) | C₁₇H₁₈FN₃O₂ C: 64.75 H: 5.75 N: 13.33 C: 64.93 H: 5.73 N: 13.28 |
| 7 | 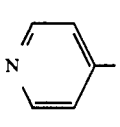 | H | 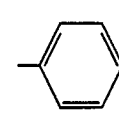 | O | O | 230~231° C. (n-C₆H₁₄:AcOEt) | C₁₇H₁₈BrN₃O₂ C: 54.27 H: 4.82 N: 11.17 C: 54.28 H: 4.70 N: 11.09 |
| 8 | 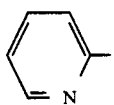 | H | 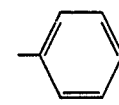 | O | O | 155~156° C. (n-C₆H₁₄:AcOEt) | C₁₇H₁₈ClN₃O₂ C: 61.54 H: 5.47 N: 12.66 C: 61.43 H: 5.47 N: 12.62 |
| 9 | 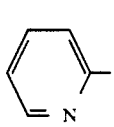 | H | 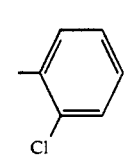 | O | O | Oil | m/e = 332 (M⁺ + 1), 205, 78 |

-continued

| Example | Ar | R¹ | R² | X | Y | M.P. (Solv.) | ANAL. [Calcd. (%)/Found (%)] or Mass (m/e) |
|---|---|---|---|---|---|---|---|
| 10 | 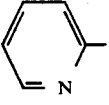 | H | 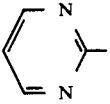 | O | O | 147~148° C. (n-C₆H₁₄:AcOEt:EtOH) | $C_{21}H_{21}N_3O_2$<br>C: 72.60 H: 6.09 N: 12.10<br>C: 72.42 H: 6.19 N: 11.99 |
| 11 | 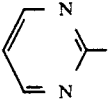 | H | 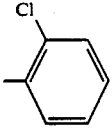 | O | O | 123~124° C. (n-C₆H₁₄:AcOEt) | $C_{16}H_{17}ClN_4O_2$<br>C: 57.75 H: 5.15 N: 16.84<br>C: 57.68 H: 5.15 N: 16.72 |
| 12 | 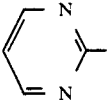 | H | Cl 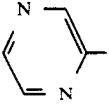 | O | O | 99~100° C. (n-C₆H₁₄:AcOEt) | $C_{16}H_{17}ClN_4O_2$<br>C: 57.75 H: 5.15 N: 16.84<br>C: 57.70 H: 5.15 N: 16.57 |
| 13 | 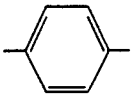 | H | 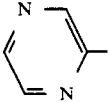 | O | O | 192~193° C. (n-C₆H₁₄:AcOEt:EtOH) | $C_{20}H_{20}N_4O_2$<br>C: 68.95 H: 5.79 N: 16.08<br>C: 68.65 H: 5.73 N: 15.85 |
| 14 | 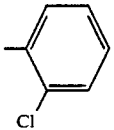 | H | 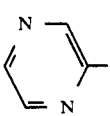 | O | O | 158~159° C. (n-C₆H₁₄:AcOEt:EtOH) | $C_{16}H_{17}ClN_4O_2$<br>C: 57.75 H: 5.15 N: 16.84<br>C: 57.62 H: 5.17 N: 16.74 |
| 15 | 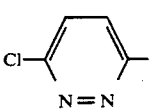 | H | 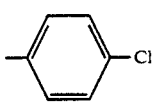 | O | O | 112~113° C. (n-C₆H₁₄:AcOEt) | $C_{16}H_{17}ClN_4O_2$<br>C: 57.75 H: 5.15 N: 16.84<br>C: 57.79 H: 5.07 N: 16.79 |
| 16 | 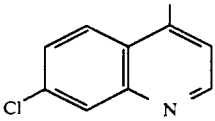 | H | 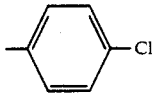 | O | O | 148° C. (n-C₆H₁₄:AcOEt:EtOH) | $C_{20}H_{20}N_4O_2$<br>C: 68.95 H: 5.79 N: 16.08<br>C: 68.64 H: 5.78 N: 15.73 |
| 17 |  | H |  | O | O | 187~188° C. (n-C₆H₁₄:EtOH) | $C_{16}H_{16}Cl_2N_4O_2$<br>C: 52.33 H: 4.39 N: 15.26<br>C: 52.30 H: 4.34 N: 15.19 |
| 18 |  | H |  | O | O | 199~200° C. (MeCN:DMF) | $C_{21}H_{19}Cl_2N_3O_2$<br>C: 60.59 H: 4.60 N: 10.09<br>C: 60.59 H: 4.54 N: 10.18 |

-continued

| Example | Ar | R¹ | R² | X | Y | M.P. (Solv.) | ANAL. [Calcd. (%)/Found (%)] or Mass (m/e) |
|---|---|---|---|---|---|---|---|
| 19 | 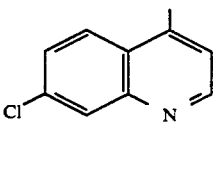 | H | 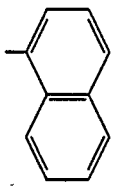 | O | O | 200~201° C. (MeCN:DMF) | $C_{25}H_{22}ClN_3O_2$<br>C: 69.52 H: 5.13 N: 9.73<br>C: 69.44 H: 5.05 N: 9.84 |
| 20 | 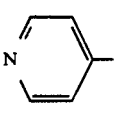 | H | 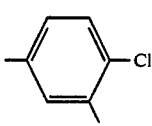 | O | O | 248~250° C. (EtOH wash) | $C_{17}H_{17}Cl_2N_3O_2$<br>C: 55.75 H: 4.68 N: 11.47<br>C: 55.66 H: 4.50 N: 11.45 |
| 21 | 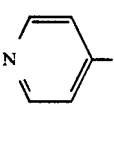 | H | 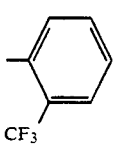 | O | O | 136~138° C. ($C_6H_6$:n-$C_6H_{14}$) | $C_{18}H_{18}F_3N_3O_2$<br>C: 59.17 H: 4.97 N: 11.50<br>C: 59.46 H: 4.90 N: 11.52 |
| 22 | 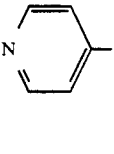 | H | 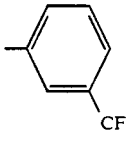 | O | O | 198~200° C. (MeCN) | $C_{18}H_{18}F_3N_3O_2$<br>C: 59.17 H: 4.97 N: 11.50<br>C: 59.14 H: 4.91 N: 11.57 |
| 23 | 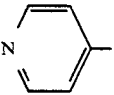 | H | 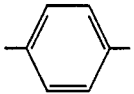 | O | O | 241~244° C. (i-PrOH) | $C_{18}H_{18}F_3N_3O_2 \cdot 1/10H_2O$<br>C: 58.88 H: 5.00 N: 11.50<br>C: 58.82 H: 4.88 N: 11.45 |
| 24* | 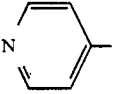 | H |  | O | O | 259~261° C. (i-PrOH) | $C_{18}H_{18}F_3N_3O_2 \cdot HCl \cdot H_2O$<br>C: 51.50 H: 5.04 N: 10.01<br>C: 51.55 H: 4.79 N: 9.92 |
| 25 | 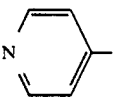 | H | 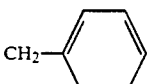 | O | O | Oil | m/e = 311 (M⁺), 178, 160, 133, 91 |
| 26 | 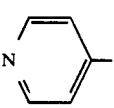 | H | 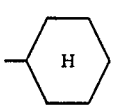 | O | O | 127~128° C. (n-$C_6H_{14}$ wash) | $C_{17}H_{25}N_3O_2 \cdot 1/5H_2O$<br>C: 66.51 H: 8.34 N: 13.69<br>C: 66.50 H: 8.34 N: 13.76 |
| 27 | 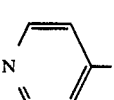 | H | 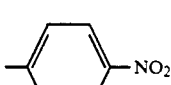 | O | O | 238~241° C. (MeOH) | $C_{17}H_{18}N_4O_4$<br>C: 59.64 H: 5.30 N: 16.37<br>C: 59.44 H: 5.19 N: 16.29 |
| 28* | 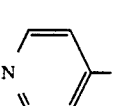 | H | 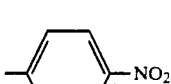 | O | O | 267~270° C. ($H_2O$) | $C_{17}H_{18}N_4O_4 \cdot HCl \cdot 1/5H_2O$<br>C: 53.39 H: 5.11 N: 14.65<br>C: 53.33 H: 4.97 N: 14.71 |
| 29 | 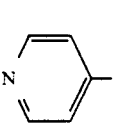 | H | 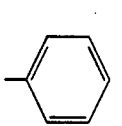 | O | S | 194~195° C. (EtOH) | $C_{17}H_{19}N_3OS$<br>C: 65.15 H: 6.11 N: 13.41<br>C: 65.24 H: 6.04 N: 13.47 |

-continued

| Example | Ar | R¹ | R² | X | Y | M.P. (Solv.) | ANAL. [Calcd. (%)/Found (%)] or Mass (m/e) |
|---|---|---|---|---|---|---|---|
| 30 | 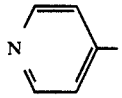 | H | 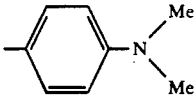 | O | O | 217~218° C. (AcOEt:EtOH) | $C_{19}H_{24}N_4O_2.1/5H_2O$<br>C: 66.33 H: 7.15 N: 16.29<br>C: 66.45 H: 7.22 N: 16.23 |
| 31 | 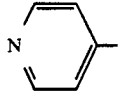 | H | 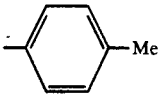 | O | O | 224~225° C. (MeCN:EtOH) | $C_{18}H_{21}N_3O_2.1/10H_2O$<br>C: 69.03 H: 6.76 N: 13.42<br>C: 69.05 H: 6.80 N: 13.47 |
| 32 | 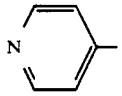 | H | 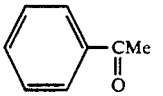 | O | O | 259~260° C. (AcOEt:EtOH) | $C_{19}H_{21}N_3O_3.1/2H_2O$<br>C: 65.50 H: 6.36 N: 12.06<br>C: 65.78 H: 6.27 N: 11.93 |
| 33 | 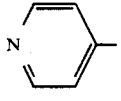 | H | 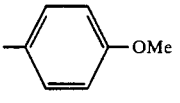 | O | O | 218~219° C. (AcOEt:EtOH) | $C_{18}H_{21}N_3O_3.1/5H_2O$<br>C: 65.32 H: 6.52 N: 12.70<br>C: 65.41 H: 6.43 N: 12.72 |
| 34 | 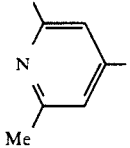 | H | 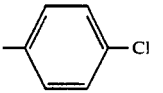 | O | O | 235~238° C. (AcOEt wash) | $C_{19}H_{22}ClN_3O_2.3/10H_2O$<br>C: 62.48 H: 6.24 N: 11.50<br>C: 62.50 H: 6.09 N: 11.38 |
| 35 | 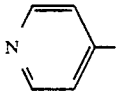 | H | 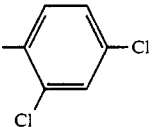 | O | O | 183~184° C. (EtOH) | $C_{17}H_{17}Cl_2N_3O_2$<br>C: 55.75 H: 4.68 N: 11.47<br>C: 55.72 H: 4.56 N: 11.37 |
| 36 | 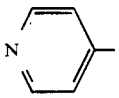 | H | 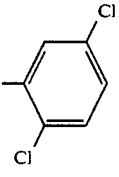 | O | O | 162~163° C. (MeCN) | $C_{17}H_{17}Cl_2N_3O_2$<br>C: 55.75 H: 4.68 N: 11.47<br>C: 55.97 H: 4.54 N: 11.68 |
| 37 | 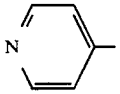 | H | 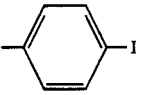 | O | O | 228~229° C. (AcOEt wash) | $C_{17}H_{18}IN_3O_2.7/10H_2O$<br>C: 46.85 H: 4.49 N: 9.64<br>C: 46.55 H: 4.15 N: 9.32 |
| 38 | 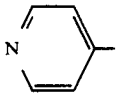 | H | 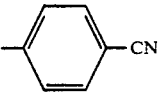 | O | O | 208~209° C. (AcOEt-MeCN-EtOH) | $C_{18}H_{18}N_4O_2.H_2O$<br>C: 63.50 H: 5.93 N: 16.47<br>C: 63.45 H: 6.14 N: 16.83 |
| 39 | 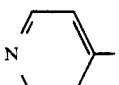 | H | 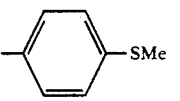 | O | O | 228~229° C. (AcOEt wash) | $C_{18}H_{21}N_3O_2S.1/5H_2O$<br>C: 62.30 H: 6.22 N: 12.11<br>C: 62.33 H: 6.20 N: 11.86 |
| 40 | 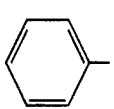 | H | 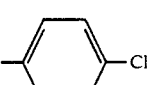 | O | O | 183~184° C. (MeCN:DMF) | m/e = 330 (M⁺), 177, 153 |

-continued

| Example | Ar | R¹ | R² | X | Y | M.P. (Solv.) | ANAL. [Calcd. (%)/Found (%)] or Mass (m/e) |
|---|---|---|---|---|---|---|---|
| 41 | 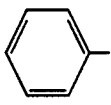 | H | 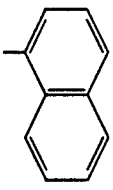 | O | O | 124~125° C. (n-C₆H₁₄:AcOEt) | $C_{22}H_{22}N_2O_2$<br>C: 76.28 H: 6.40 N: 8.09<br>C: 76.17 H: 6.40 N: 8.06 |
| 42 | 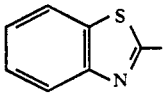 | H | 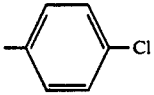 | O | O | 152~153° C. (n-C₆H₁₄:AcOEt:EtOH) | $C_{19}H_{18}ClN_3O_2S$<br>C: 58.83 H: 4.68 N: 10.83<br>C: 58.99 H: 4.63 N: 10.80 |
| 43 | 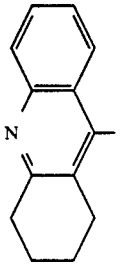 | H |  | O | O | 203° C. (n-C₆H₁₄:EtOH) | $C_{25}H_{26}ClN_3O_2$<br>C: 68.88 H: 6.01 N: 9.64<br>C: 68.53 H: 5.89 N: 9.62 |
| 44 | 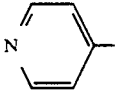 | H | 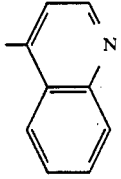 | O | O | 271~273° C. (MeOH) | $C_{20}H_{20}N_4O_4$<br>C: 68.95 H: 5.79 N: 16.08<br>C: 68.88 H: 5.64 N: 16.09 |
| 45 | 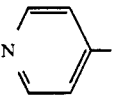 | H | 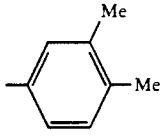 | O | O | 191~192° C. (i-prOH) | $C_{19}H_{23}N_3O_2$<br>C: 70.13 H: 7.12 N: 12.91<br>C: 69.91 H: 7.15 N: 13.01 |
| 46 | 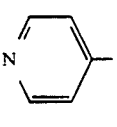 | H | 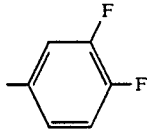 | O | O | 211~212° C. (MeCN) | $C_{17}H_{17}F_2N_3O_2$<br>C: 61.26 H: 5.14 N: 12.61<br>C: 61.13 H: 5.05 N: 12.78 |
| 47 | 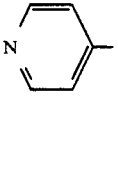 | H | 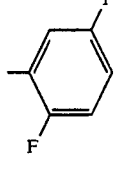 | O | O | 195~196° C. (MeCN) | $C_{17}H_{17}F_2N_3O_2$<br>C: 61.26 H: 5.14 N: 12.61<br>C: 61.06 H: 5.01 N: 12.83 |
| 48 | 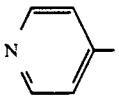 | H | 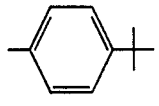 | O | O | 220~221° C. (MeOH) | $C_{21}H_{27}N_3O_2$<br>C: 71.36 H: 7.70 N: 11.89<br>C: 71.26 H: 7.76 N: 12.07 |

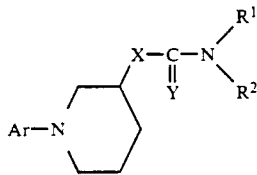

| Example | Ar | R¹ | R² | X | Y | M.P. (Solv.) | ANAL. [Calcd. (%)/Found (%)] or Mass (m/e) |
|---|---|---|---|---|---|---|---|
| 49 | 3-pyridyl | H | 4-Cl-C₆H₄ | O | O | 183~184° C. (MeCN) | $C_{17}H_{18}ClN_3O_2$<br>C: 61.54 H: 5.47 N: 12.66<br>C: 61.38 H: 5.38 N: 12.62 |
| 50 | 3-pyridyl | H | 4-Me-C₆H₄ | O | O | 163~165° C. (MeCN) | $C_{18}H_{21}N_3O_2$<br>C: 69.43 H: 6.80 N: 13.50<br>C: 69.53 H: 6.80 N: 13.51 |
| 51 | 3-pyridyl | H | 4-F-C₆H₄ | O | O | 169~196° C. (MeCN) | $C_{17}H_{18}FN_3O_2$<br>C: 64.75 H: 5.75 N: 13.33<br>C: 64.59 H: 5.71 N: 13.34 |
| 52 | 3-pyridyl | H | 3-CF₃-C₆H₄ | O | O | 194~196° C. (MeCN) | $C_{18}H_{18}F_3N_3O_2$<br>C: 59.17 H: 4.97 N: 11.50<br>C: 59.27 H: 4.91 N: 11.58 |
| 53 | 3-pyridyl | H | 4-C(O)Me-C₆H₄ | O | O | 173~175° C. (AcOEt:n-C₆H₁₄) | $C_{19}H_{24}N_3O_3$<br>C: 67.24 H: 6.24 N: 12.38<br>C: 66.97 H: 6.24 N: 12.26 |
| 54 | 3-pyridyl | H | 4-NMe₂-C₆H₄ | O | O | 134~136° C. (AcOEt:n-C₆H₁₄) | $C_{19}H_{24}N_4O_2$<br>C: 67.04 H: 7.11 N: 16.46<br>C: 66.92 H: 7.17 N: 16.52 |
| 55 | 3-pyridyl | H | 3,4-(OMe)₂-C₆H₃ | O | O | Oil | $C_{19}H_{23}N_3O_4 \cdot 2/5H_2O$<br>C: 62.59 H: 6.58 N: 11.52<br>C: 62.43 H: 6.49 N: 11.64 |
| 56 | 3-pyridyl | H | 4-OMe-C₆H₄ | O | O | 176~178° C. (MeCN) | $C_{18}H_{21}N_3O_3$<br>C: 66.04 H: 6.47 N: 12.84<br>C: 66.86 H: 6.42 N: 12.94 |

*Hydrochloride

Example 57

(R)-(+)-3-piperidyl 4-chlorophenycarbamate (1) Two steps synthesis (a) Into a solution of (R)-(−)-N-tert-butoxycarbonyl-3-piperidinol (Reference Example 2) (23 g) in dry tetrahydrofuran (20 ml) were added 4-chlorophenyl isocyanate (1.43 ml) and triethylamine (1.87 mi) successively at room temperature with stirring, and then the mixture was stirred at room temperature for 10 hours. The reaction mixture was distilled under reduced pressure to give residues which was adsorbed on ca. 20 g of silica gel with employment of 50 ml of methylene chloride and purified through column chromatography (alumina, n-hexane:ethyl acetate =5:1) to give (R)-(+)-N-tert-butoxycarbonyl-3-piperidyl 4-chlorophenylcarbamate (3.07 g) of colorless prism crystal.

Melting point 160°-161° C.
Elementary analysis (%) for $C_{17}H_{23}ClN_2O_4$:
Calculated value C: 57.54, H: 6.53, N: 7.89.
Observed value C: 57.66, H: 6.55, N: 7.83.
$[\alpha]_D^{25}$ 46.76° (1=100, c 1.0, ethanol)

(b) Into a solution of the compound obtained (2.7 g) in (a) step in tetrahydrofuran (50 mi) was added 2.4N-hydrochloric acid (20 mi) at room temperature with stirring and the mixture was refluxed with heating for 5 hours. The reaction mixture was concentrated under reduced pressure, added with ca. 50 ml of hot water and insoluble matter was removed by filtration to give filtrate. The filtrate was made to have PH value of more than 11 with gradual addition of potassium hydroxide under ice cooling with stirring and extracted with ethyl acetate.

The organic layer was washed with saturated aqueous sodium chloride solution to give a residue (1.18 g), which was then azeotropically twice boiled with a little amount of acetonitrile added and was recrystallized from acetonitrile to afford the title compound (1.43 g) of colorless prism crystal.

Melting point 144°-145° C.

Elementary analysis (%) for $C_{12}H_{15}ClN_2O_2$:
Calculated value C: 56.59, H: 5.94, N: 11.00.
Observed value C: 56.57, H: 5.92, N: 11.10.

$[\alpha]_D^{25}$ 17.47° (1=100, c 1.0, ethanol)

(2) One step synthesis

Into a solution of (R)-(−)-N-tert-butoxycarbonyl-3-piperidinol (Reference Example 2) (7.91 g) in dry tetrahydrofuran (60 ml) were successively added 4-chlorophenyl isocyanate (5.03 ml) and triethylamine (6.57 ml) at room temperature with stirring, and thereafter the mixture was stirred at room temperature for 10 hours. The reaction mixture was distilled off under reduced pressure to give residue, which was then dissolved into tetrahydrofuran (120 ml) added and was refluxed with heating for 7 hours after addition of 2.4N-hydrochloric acid (70 ml) at room temperature. The reaction mixture was concentrated under reduced pressure, added with ca. 100 ml of hot water and the resulted insoluble matter was removed by filtration to give filtrate. To this filtrate was slowly added with potassium hydroxide under ice cooling with stirring to have pH value of more than 11, and was stirred, as it was, under ice cooling for 1 hour and further at room temperature for 1 hour. The precipitated crystal was collected through filtration and this crystal was recrystallized from acetonitrile to give the title compound (7.3 g) as colorless prism crystal, the spectrum data of which accorded with those obtained in (1).

Example 58

(R)-(−)-[3-(1-(4-pyridyl)piperidyl)] 4-chlorophenylcarbamate

Into a solution of (R)-(+)-3-piperidyl 4-chlorophenylcarbamate (Example 57) (9.3 g) in isoamyl alcohol (170 ml) were successively added 4-chloropyridine hydrochloride(6.02 g), sodium hydrogen carbonate (4.6 g) and sodium acetate (3.59 g) at room temperature, and after stirred as it was at room temperature for 30 minutes, the mixture was added with sodium iodide (6.02 g) and refluxed with stirring for 4 hours. The reaction mixture was subjected to celite filtration to remove inorganic matter and this inorganic matter was washed with ethyl acetate, which was then combined with the former filtrate. The filtrate was washed with saturated sodium hydrogen carbonate and the organic layer was separated, while the aqueous layer was again extracted with ethyl acetate. The organic layers were combined, dried over anhydrous sodium sulfate, the solvent thereof was distilled off under reduced pressure and the obtained residue was azeotropically boiled with toluene to give a semi-solid matter. This was purified through column chromatography (alumina, methylene chloride) and fractions including the aimed compound were collected to give oily matter by distillation off of the solvent, which was then dissolved with addition of acetonitrile and crystallized by distillation of the solvent. This crude crystal was recrystallized from acetonitrile to give the title compound (5.49 g) as colorless prism crystal.

Melting point 144°–145° C.
Elementary analysis (%) for $C_{17}H_{18}ClN_3O_2$:
Calculated value C: 61.54, H: 5.47, N: 12.66.
Observed value C: 61.45, H: 5.38, N: 12.66.

$[\alpha]_D^{25}$ −29.11° (1=50, c 1.1, ethyl acetate)

Example 59

(S)-(−)-3-piperidyl 4-chlorophenylcarbamate (1) Two steps synthesis

Likewise as in Example 57(1)-a, from (S)-(+)-N-tert-butoxycarbonyl-3-piperidinol (Reference Example 4) was obtained (S)-(−)-N-tert-butoxycarbonyl-3-piperidyl 4-chlorophenylcarbamate (2.58 g) as colorless prism crystal.

Melting point 161°–162° C.
Elementary analysis for $C_{17}H_{23}ClN_2O_4$:
Calculated value C: 57.54, H: 6.53, N: 7.89.
Observed value C: 57.73, H: 6.57, N: 7.90.

$[\alpha]_D^{25}$ −46.56° (1=100, c=1.0, ethanol)

Further, likewise as in Example 57(1)-b, from the obtained compound (2.3 g) was obtained the title compound (1.07 g) as colorless prism crystal.

Melting point 143°–144° C.
Elementary analysis for $C_{12}H_{15}ClN_2O_2$:
Calculated value C: 56.59, H: 5.94, N: 11.00.
Observed value C: 56.60, H: 5.91, N: 11.11.

$[\alpha]_D^{25}$ −17.21° (1=100, c 1.0, ethanol)

(2) One step synthesis

Likewise as in Example 57(2), from (S)-(+)-N-tert-butoxycarbonyl-3-piperidinol (Reference Example 4) (9.3 g) was obtained the title compound (9.48 g) as colorless prism crystal.

The spectrum data thereof accorded with those obtained in (1).

Example 60

(S)-(+)-[3-(1-(4-pyridyl)piperidyl)] 4-chlorophenylcarbamate

With employment of (S)-(−)-3-piperidyl 4-chlorophenylcarbamate (Example 59) (9.5 g), 4-chloropyridine hydrochloride (6.2 g), sodium hydrogen carbonate (4.7 g), sodium acetate (3.67 g), sodium iodide (6.15 g) and isoamyl alcohol (150 ml), likewise as in Example 58, was obtained the title compound (6.81 g) as colorless prism crystal.

Melting point 143°–144° C.
Elementary analysis (%) for $C_{17}H_{18}ClN_3O_2$:
Calculated value C: 61.54, H: 5.47, N: 12.66.
Observed value C: 61.60, H: 5.41, N: 12.69.

$[\alpha]_D^{25}$ 28.48° (1=50, c 1.02, ethyl acetate)

Reference Example 1

(R)-(+)-3-piperidinol (L)-(+)-4-chlorophenyl tartaric acid amide salt

According to the method described in J. Med. Chem., 15, 1085 (1972) and Eur. J. Med. Chem., 11, 461 (1976), from (±)-3-piperidinol was obtained the title compound as colorless heedle crystal.

Melting point 153°–155° C.
Elementary analysis for $C_{15}H_{20}ClN_2O_6 \cdot H_2O$:
Calculated value C: 47.56, H: 6.12, N: 7.40.
Observed value C: 47.77, H: 6.12, N: 7.49.

$[\alpha]_D^{25}$ 78.07° (1=100, c 0.75, distilled water)

Reference Example 2

(R)-(−)-N-tert-butoxycarbonyl-3-piperidinol

Into a suspension of the compound (37.88 g) synthesized in the Reference Example (1) in a mixture (300 ml) of methylene chloride:methanol (1:1) were successively added diiso-propylethylamine (38.41 ml) and a solution of di-tertbutyl dicarbonate (22.91 g) in methylene chloride (50 ml) at room temperature with stirring.

After stirred at room temperature for 3 hours, the mixture was distilled off under reduced pressure to give residue, which was then dissolved into methylene chloride (300 ml). This organic layer was washed twice with saturated aqueous solution of sodium hydrogen carbonate and once with saturated aqueous solution of sodium chloride to give residue. This was purified through column chromatography (silica gel, n-hexane:ethyl acetate=1:2) and further the solvent was distilled under reduced pressure (200° C./0.7 mm Hg) to give the title compound (21.03 g) as colorless oily product.

Elementary analysis for $C_{10}H_{19}NO_3$:
Calculated value C: 59.68, H: 9.52, N: 6.96.
Observed value C: 59.50, H: 9.72, N: 6.99.

$[\alpha]_D^{25}$ −22.89° (1=50, c 1.7, ethanol)

Reference Example 3

(S)-(−)-3-piperidinol (D)-(−)-4-chlorophenyl tartaric acid amide salt

According to the method described in J. Med. Chem., 15, 1085 (1972) and Eur. J. Med. Chem., 11, 461 (1976), from (±)-3-piperidinol was synthesized the title compound as colorless needle crystal.

Melting point 153°-154° C.
Elementary analysis for $C_{15}H_{20}ClN_2O_6 \cdot H_2O$:
Calculated value C: 47.56, H: 6.12, N: 7.40.
Observed value C: 47.31, H: 6.12, N: 7.36.

$[\alpha]_D^{25}$ −78.37° (1=50, c 0.76, distilled water)

Reference Example 4

(S)-(+)-N-tert-butoxycarbonyl-3-piperidinol

Except replacement of base, di-iso-propylethylamine in Reference Example 2 with triethylamine, with employment of the same procedure, from the optically active salt (17.7 g) synthesized in Reference Example 3 was obtained the title compound (9.36 as colorless oily product.

Elementary analysis for $C_{10}H_{19}NO_3$.
Calculated value C: 59.68, H: 9.52, N: 6.96.
Observed value C: 59.49, H: 9.70, N: 6.98.

$[\alpha]_D^{25}$ 23.48° (1=50, c 1.6, ethanol)

Experiment

Action against amnesia induced by exposure to carbon dioxide gas

The experimental animals employed were the Std: ddy strain male mice (Japanese SLC) having body weight of 23-32 g (five weeks old). The apparatus used was a passive avoidance apparatus of a step-through type (made by O'Hara Co., Ltd.). In the aquisition trial, each mouse was placed in the light compartment, a guillotine door of partition thereof was opened after 10 seconds, the guillotine door was closed as soon as the mouse moved into the dark compartment and an electric shock of 33-50 v was given for 1 second through the metal grid bars of the floor. Immediately after the electric shock was given, the mouse was taken out and was accommodated in a container having volume of ca. 300 ml filled with carbon dioxide gas. After immediately exposed to carbon dioxide gas having flow rate of ca. 5 liter/min. for 25-45 seconds, the mouse was taken out and was reanimated by artificial breathing. The retention trial was carried out after 24 hours. In the retention trial, the mouse was again placed in the light compartment, the time till the movement to the dark compartment was measured as a reaction latency until maximum 300 seconds and the mouse showing latency beyond it was deemed as 300 seconds. In addition, immediately after aquisition trial, a group not to exposed to carbon dioxide gas (comparison group of non-amnesia) was also made. The mouse was grouped per 10-30, the subject medicament was orally administered immediately after exposed to carbon dioxide gas and one hour before the retention trial. The amelioration rate was calculated according to the following equation and the result was shown in Table 1.

Rate of improvement =

$$\frac{\text{Latency of } CO_2\text{-drug treated group} - \text{Latency of carbon dioxide exposed group}}{\text{Latency of non-dementia group} - \text{Latency of carbon dioxide exposed group}} \times 100$$

Effect on amnesia induced by carbon dioxide

| Compound | Dose (mg/kg) | Number of animal | Reaction latency (sec) Means ± S.E. | Rate of improvement (%) |
|---|---|---|---|---|
| Non-treated | — | 20 | 278.5 ± 12.0 | 42.9 |
| CO2 treated mouse | — | 20 | 54.8 ± 15.2 | |
| Example 2 | 10 | 20 | 150.7 ± 27.1** | |
| Non-treated | — | 30 | 269.7 ± 12.1 | 76.8 |
| CO2 treated mouse | — | 30 | 103.6 ± 18.5 | |
| Example 2 | 30 | 30 | 231.2 ± 19.0** | |
| Non-treated | — | 20 | 300.0 ± 0 | 45.3 |
| CO2 treated mouse | — | 20 | 87.3 ± 18.9 | |
| Example 49 | 10 | 20 | 154.0 ± 27.2 | |
| | 30 | 20 | 183.7 ± 26.3** | |
| Non-treated | — | 10 | 300.0 ± 26.3** | −59.8 |
| CO2 treated mouse | — | 10 | 170.4 ± 26.3** | |
| Nicardipine | 5 | 10 | 92.9 ± 26.3**28.1 | |
| Non-treated | — | 19 | 282.5 ± 12.1 | 37.9 |
| CO2 treated mouse | — | 20 | 131.1 ± 23.9 | |
| Bifemelane | 100 | 19 | 188.5 ± 27.1 | |
| Non-treated | — | 30 | 300.0 ± 0 | 30.1 |
| CO2 treated mouse | — | 30 | 184.5 ± 18.3 | |
| Indeloxazine | 40 | 30 | 219.3 ± 17.8 | |
| Non-treated | — | 10 | 300.0 ± 0 | 15.2 |
| CO2 treated mouse | — | 10 | 152.9 ± 37.8 | |
| Compound A | 100 | 10 | 175.3 ± 36.7 | |

*: $P < 0.05$, **: $P < 0.01$ There is a significant difference to $CO_2$ treated group
Compound A: 3-(1-methylpiperidinyl) phenylcarbamate (Egypt. J. Pharm. Sci., 26. 267(1985))

As mentioned above, the carbamic acid derivatives of the present invention show excellent improving activity to disturbance of memory while the improving activity to disturbance of memory of the conventional treatment medicament to cerebrovascular disturbance (Nicardipine)and the conventional activating medicament to cerebral metabolism (Bifemelane, Indeloxazine) is vitiated or not enough. Accordingly, the compounds of the present invention are effective as anti-dementia medicament.

What is claimed is:

1. A carbamic acid represented by formula (I)

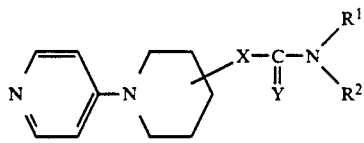

wherein $R^1$ denotes hydrogen atom or lower alkyl group, $R^2$ denotes lower alkyl group which may be substituted with halogen atom, phenyl group which may have at least one substituent, naphthyl group, or five- or six-membered heterocyclic ring or its benzene-condensed ring, and X and Y, being same or different, denote sulfur atom or oxygen atom or their acid addition salts.

2. An anti-dementia composition comprising an effective amount of at least one of the carbamic acids represented by formula (I)

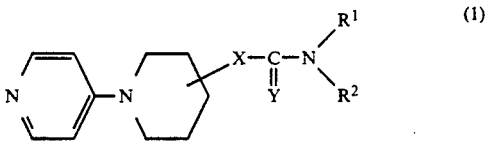

wherein $R^1$ denotes hydrogen atom or lower alkyl group, $R^2$ denotes lower alkyl group which may be substituted with halogen atom, phenyl group which may have at least one substituent, naphthyl group, or five- or six-membered heterocyclic ring or its benzene-condensed ring, and X and Y, being same or different, denote sulfur atom or oxygen atom or their acid addition salts, in combination with a pharmaceutically suitable carrier.

* * * * *

UNITED STATES PATENT AND TRADEMARK OFFICE
CERTIFICATE OF CORRECTION

PATENT NO. : 5,300,515
DATED : April 5, 1994
INVENTOR(S) : Yasuo TAKANO, et al.

It is certified that error appears in the above-indentified patent and that said Letters Patent is hereby corrected as shown below:

On the title page, Item [30], the 2nd Foreign Application Priority Data has been omitted and should read as follows:

--Jan. 21, 1992 [JP] Japan .................... 4-030071--

Signed and Sealed this

Twenty-sixth Day of July, 1994

Attest:

BRUCE LEHMAN

*Attesting Officer*      *Commissioner of Patents and Trademarks*